(12) United States Patent
Igarashi

(10) Patent No.: US 12,309,479 B2
(45) Date of Patent: May 20, 2025

(54) IMAGE PICKUP MODULE AND ENDOSCOPE

(71) Applicant: OLYMPUS CORPORATION, Tokyo (JP)

(72) Inventor: Takatoshi Igarashi, Nagano (JP)

(73) Assignee: OLYMPUS CORPORATION, Tokyo (JP)

( * ) Notice: Subject to any disclaimer, the term of this patent is extended or adjusted under 35 U.S.C. 154(b) by 620 days.

(21) Appl. No.: 17/534,861

(22) Filed: Nov. 24, 2021

(65) Prior Publication Data

US 2022/0079428 A1 Mar. 17, 2022

Related U.S. Application Data

(63) Continuation of application No. PCT/JP2019/037985, filed on Sep. 26, 2019.

(51) Int. Cl.
*A61B 1/00* (2006.01)
*A61B 1/05* (2006.01)
*H04N 23/50* (2023.01)
*H04N 23/55* (2023.01)
*H04N 23/57* (2023.01)

(52) U.S. Cl.
CPC ......... *H04N 23/57* (2023.01); *A61B 1/00188* (2013.01); *A61B 1/05* (2013.01); *H04N 23/555* (2023.01)

(58) Field of Classification Search
CPC ... A61B 1/05; A61B 1/00188; A61B 1/00096; H04N 23/55; H04N 23/57; H04N 23/555
See application file for complete search history.

(56) References Cited

U.S. PATENT DOCUMENTS

| 2010/0053402 A1* | 3/2010 | Itakura | H04N 25/767 348/340 |
| 2018/0049627 A1* | 2/2018 | Adachi | G02B 23/26 |

(Continued)

FOREIGN PATENT DOCUMENTS

| JP | S63-259507 A | 10/1988 |
| JP | 2007-228296 A | 9/2007 |

(Continued)

OTHER PUBLICATIONS

International Search Report dated Nov. 26, 2019 received in PCT/JP2019/037985.
English abstract only of WO 2013/091123 A1.

*Primary Examiner* — Anh Tuan T Nguyen
*Assistant Examiner* — Rynae E Boler
(74) *Attorney, Agent, or Firm* — Scully, Scott, Murphy & Presser, P.C.

(57) ABSTRACT

An image pickup module includes an image pickup device having a light receiving circuit, a prism arranged on the light receiving circuit and configured to bend incident light to guide the incident light to the light receiving circuit, a stacked device that includes a plurality of semiconductor devices each having a through wiring and bonded to each other by solder, and is arranged around the light receiving circuit of the image pickup device, a resin layer stacked on an uppermost semiconductor device of the plurality of semiconductor devices of the stacked device, and a plurality of cables connected to the stacked device and having a connection portion with the stacked device covered with the resin layer.

14 Claims, 6 Drawing Sheets

(56) References Cited

U.S. PATENT DOCUMENTS

| | | | | |
|---|---|---|---|---|
| 2019/0069767 A1* | 3/2019 | Mikami | ............ | H01L 27/14636 |
| 2019/0175003 A1* | 6/2019 | Yoshida | ................. | H04N 23/57 |
| 2019/0214426 A1* | 7/2019 | Shimohata | ........ | H01L 27/14618 |

FOREIGN PATENT DOCUMENTS

| | | | | |
|---|---|---|---|---|
| JP | 2010-051538 A | 3/2010 | | |
| JP | 2013-211697 A | 10/2013 | | |
| JP | 2015-508299 A | 3/2015 | | |
| JP | 2015-198726 A | 11/2015 | | |
| JP | 2017-192752 A | 10/2017 | | |
| JP | 2019-141485 A | 8/2019 | | |
| WO | 2016/203828 A1 | 12/2016 | | |
| WO | WO-2017199406 A1 * | 11/2017 | ......... | A61B 1/00114 |
| WO | WO-2018078765 A1 * | 5/2018 | ........... | A61B 1/0008 |
| WO | WO-2018078766 A1 * | 5/2018 | ........... | A61B 1/0011 |
| WO | 2018/193531 A1 | 10/2018 | | |
| WO | 2018/198247 A1 | 11/2018 | | |

\* cited by examiner

IMAGE PICKUP MODULE AND ENDOSCOPE

CROSS REFERENCE TO RELATED APPLICATION

This application is a continuation application of PCT/JP2019/037985 filed on Sep. 26, 2019, the entire contents of which are incorporated herein by this reference.

BACKGROUND OF THE INVENTION

1. Field of the Invention

The present invention relates to an image pickup module and an endoscope including the image pickup module.

2. Description of the Related Art

Development of an ultra-small image pickup module has been advanced, for example, in order to achieve a less-invasive endoscope.

Japanese Patent Application Laid-Open Publication No. 2015498726 discloses an endoscope in which an image pickup apparatus (image pickup module) is disposed at a distal end portion of an insertion portion. The image pickup apparatus is configured such that an image pickup device and a stacked substrate are disposed on an image pickup substrate (wiring board), and a prism is bonded to a light receiving portion of the image pickup device.

International Publication No. 2018/198247 discloses an image pickup module in which an image pickup device and a stacked device in which a plurality of semiconductor devices is stacked are disposed on a wiring board.

SUMMARY OF THE INVENTION

An image pickup module according to an embodiment of the present invention includes an image pickup device having a light receiving circuit, a prism arranged on the light receiving circuit and configured to bend incident light to guide the incident light to the light receiving circuit, a stacked device that includes a plurality of semiconductor devices each having a through wiring and bonded to each other by solder, and is arranged around the light receiving circuit of the image pickup device, a plurality of cables connected to the stacked device, and a resin layer stacked on an uppermost semiconductor device among the plurality of semiconductor devices of the stacked device, and covering a bonding portion between the plurality of cables and the stacked device.

An endoscope according to an embodiment of the present invention includes an image pickup module that includes an image pickup device having a light receiving circuit, a prism arranged on the light receiving circuit and configured to bend incident light to guide the incident light to the light receiving circuit, a stacked device that includes a plurality of semiconductor devices each having a through wiring and bonded to each other by solder, and is arranged around the light receiving circuit of the image pickup device, a plurality of cables connected to the stacked device, and a resin layer stacked on an uppermost semiconductor device among the plurality of semiconductor devices of the stacked device, and covering a bonding portion between the plurality of cables and the stacked device.

DETAILED DESCRIPTION OF THE PREFERRED EMBODIMENTS

Endoscope

Figure 1:
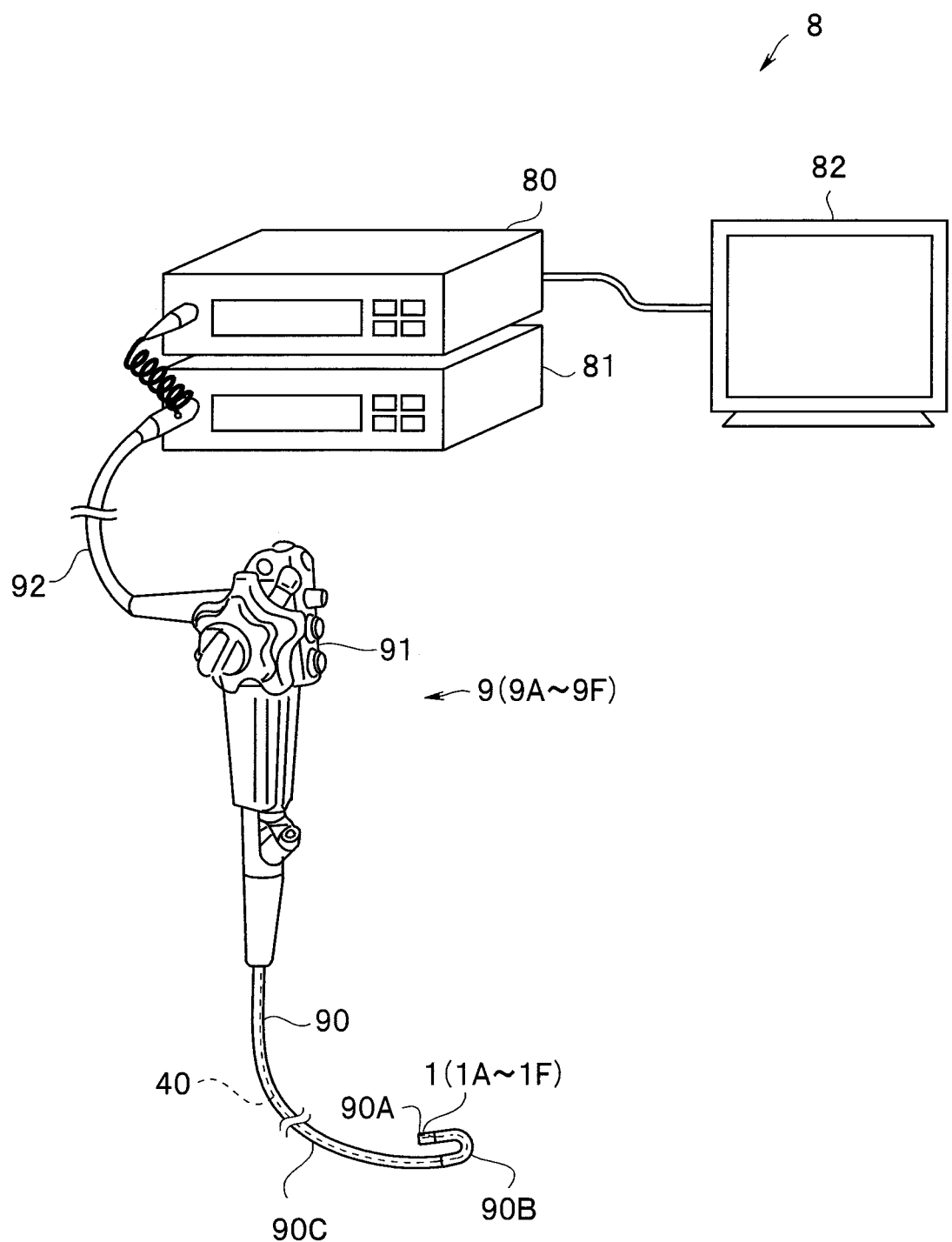
FIG. 1 is a perspective view of an endoscope system including an endoscope according to an embodiment.

As illustrated in FIG. 1, an endoscope system 8 includes an endoscope 9, a processor 80, a light source device 81, and a monitor 82. The endoscope 9 includes an insertion portion 90, an operation portion 91, and a universal cord 92. In the endoscope 9, the insertion portion 90 is inserted into a body cavity of a subject, an in-vivo image of the subject is shot, and an image signal is outputted.

The insertion portion 90 includes a distal end portion 90A in Which the image pickup module 1 is disposed, a bending portion 90B provided to be extended from the distal end portion 90A, and a flexible portion 90C provided to be extended from the bending portion 90B. A proximal end portion of the insertion portion 90 is connected to the operation portion 91 provided with various buttons for operating the endoscope 9. The bending portion 90B is bent by the operation of the operation portion 91.

The light source device 81 includes, for example, a white LED. Illumination light emitted by the light source device 81 is guided to the distal end portion 90A by passing through a light guide (not illustrated) inserted through the universal cord 92 and the insertion portion 90, and illuminates a subject.

An image pickup signal outputted by the image pickup module 1 is transmitted to the processor 80 via a cable 40 inserted through the insertion portion 90.

As will be described later, since the image pickup module 1 is extremely small (small diameter/short length), the endoscope 9 is minimally invasive.

Note that the endoscope 9 may be a rigid endoscope or may be for industrial use.

First Embodiment

Figure 2:
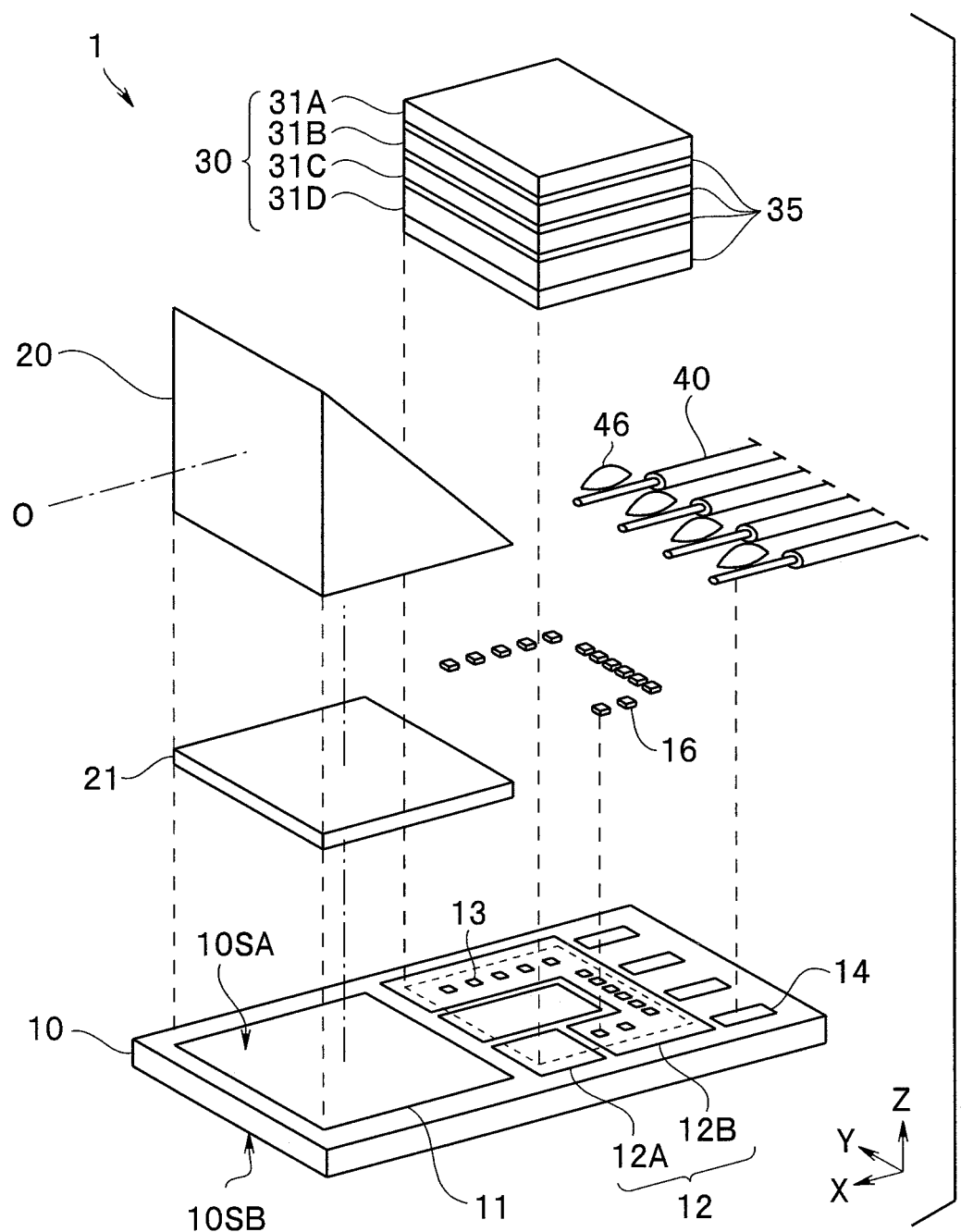
FIG. 2 is an exploded view of an image pickup module according to a first embodiment.
Figure 3:
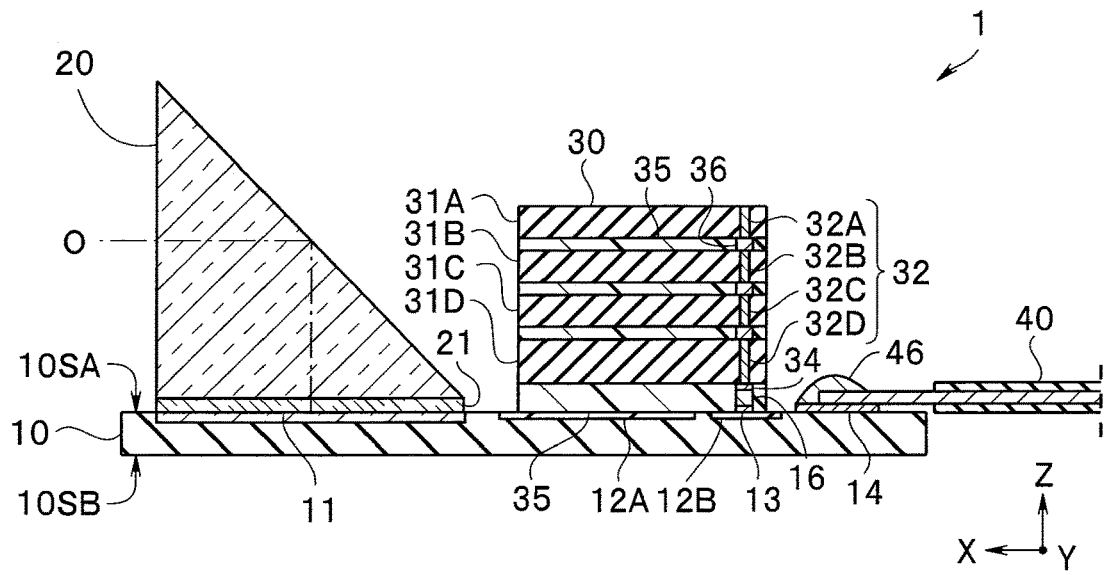
FIG. 3 is a cross-sectional view of the image pickup module according to the first embodiment.

The image pickup module 1 of the present embodiment illustrated in FIG. 2 and FIG. 3 includes an image pickup device 10, a prism 20, a stacked device 30, and a plurality of cables 40.

The drawings based on the following embodiments are schematic, and the relationship between the thickness and the width of each portion, the ratio of the thickness of each portion, the relative angle, and the like are different from the actual configuration. The drawings also include portions having mutually different dimensional relationships and ratios. Illustration of some components is omitted. The direction of the subject (X-axis increasing direction) is referred to as "front", and the opposite direction is referred to as "rear".

The image pickup device (image pickup chip) 10 that is an imager is a flat plate having a light receiving surface 10SA and a back surface 10SB opposite to the light receiving surface 10SA. A light receiving circuit 11 and a peripheral circuit 12 are formed on the light receiving surface 10SA. The image pickup device 10 having a semiconductor such as silicon as a base is a CCD or CMOS image sensor in which the light receiving circuit 11 and the peripheral circuit 12 are formed on the light receiving surface 10SA by using a known semiconductor manufacturing technology. The light receiving circuit 11 includes a plurality of light receiving pixels.

The peripheral circuit 12 arranged around the light receiving circuit 11 is, for example, a semiconductor circuit that performs primary processing on a signal outputted from the light receiving circuit 11. The peripheral circuit 12 includes an analog circuit 12A that performs an analog signal processing and a digital circuit 12B that performs a digital signal processing. The peripheral circuit 12 is formed on the rear side of the light receiving circuit 11, that is, at a position farther from the subject than the light receiving circuit 11.

On the light receiving circuit 11 of the image pickup device 10, the prism 20 is bonded by, for example, an ultraviolet curable transparent adhesive 21. Incident light condensed by an image pickup optical system 23 (see FIG. 9) including a plurality of lenses enters the prism 20 from the front along an optical axis O. The prism 20 is a right-angle prism that guides incident light to the light receiving circuit 11 by bending the incident light on a reflection surface. An entrance plane and an exit plane of the prism 20 have substantially the same size as the light receiving circuit 11, for example, 500 µm square.

A mirror may be used instead of the prism 20 as long as the optical system is an optical system that bends an optical path of incident light entering along the optical axis O (X-axis) that is a direction perpendicular to a normal direction (Z-axis direction) of the light receiving surface 10SA in a normal direction of the optical axis O.

As illustrated in FIG. 3, in the stacked device 30, a plurality of semiconductor devices (flat semiconductor chips) 31A to 31D each having silicon as a base is stacked with a sealing layer 35 interposed between the semiconductor devices. Note that when each of a plurality of components having similar functions is listed, an alphabetical character at the end of a reference numeral may be omitted. For example, each of the plurality of semiconductor devices 31A to 31D is referred to as a semiconductor device 31.

The stacked device 30 is, for example, a rectangular parallelepiped manufactured by cutting a stacked wafer in which a plurality of semiconductor device wafers is stacked. The plurality of semiconductor devices 31A to 31D has a through wiring 32 (32A to 32D), respectively, and is bonded by a solder 36.

For example, a signal processing circuit, a thin film inductor, a thin film capacitor, an analog/digital conversion circuit, or a memory circuit is formed in each of the plurality of semiconductor devices 31. The semiconductor device 31D arranged at the lowermost part of the stacked device 30 has a plurality of bonding electrodes 34.

In the image pickup device 10, two types of external electrodes including a first external electrode 13 and a second external electrode 14 are disposed on the light receiving surface 10SA.

The stacked device 30 formed by stacking the plurality of semiconductor devices 31 is arranged on the peripheral circuit 12, that is, on the rear side farther from the subject than the prism 20. The sealing layer 35 is also provided between the stacked device 30 and the image pickup device 10.

At least a part of the stacked device 30 is arranged on the peripheral circuit 12 neighboring the light receiving circuit 11 in the image pickup device 10. For example, the bonding electrode 34 on the lower surface of the stacked device 30 is bonded to the first external electrode 13 arranged on the digital circuit 12B of the image pickup device 10 by a solder 16.

When the stacked device 30 is bonded to the first external electrode 13, thermal stress and mechanical stress are applied to the peripheral circuit 12 under the stacked device 30. Since characteristics of the digital circuit 12B are less likely to change due to stresses than those of the analog circuit 12A, the first external electrode 13 to which the stacked device 30 is bonded is preferably arranged on the digital circuit 12B.

The plurality of cables 40 is bonded to the second external electrode 14 on the light receiving surface 10SA of the image pickup device 10 by, for example, a conductive paste 46.

The plurality of cables 40 may include not only electric cables for transmitting electric signals or electric power but also optical cables having optical fibers for transmitting optical signals.

In the image pickup module 1, the stacked device 30 in which a plurality of semiconductor devices having functions equivalent to those of an existing chip component or semiconductor component is stacked is arranged on the rear side of the prism 20. The image pickup module 1 has a height (Z-axis dimension) smaller than that of an existing image pickup module in which an image pickup device and a plurality of chip components and semiconductor components are disposed on a wiring board, and can be arranged in a small-diameter space. Note that since a height (dimension in the Z-axis direction) of the stacked device 30 is lower than the height of the prism 20, a height of the image pickup module 1 is not increased by disposing the stacked device 30.

Since the image pickup module 1 is configured in a state in which the stacked device 30 is arranged on the peripheral circuit 12 of the image pickup device 10, a length in the optical axis direction (X direction) is short.

As described above, the plurality of semiconductor devices 31 (31A to 31D) of the stacked device 30 is bonded by the solder 36 that is a first member. The bonding electrode 34 of the stacked device 30 is bonded to the first external electrode 13 of the image pickup device 10 by the solder 16 that is a second member. The cable 40 is bonded to the second external electrode 14 by, for example, the conductive paste 46 that is a third member.

A bonding temperature (melting point) of the solder 36 is higher than a bonding temperature (inciting point) of the solder 16. Therefore, when the stacked device 30 bonded using the solder 36 is bonded to the image pickup device 10, the solder 36 does not melt. The bonding temperature of the solder 16 is higher than a bonding temperature (curing temperature) of the conductive paste 46. Therefore, when the cable 40 is bonded to the image pickup device 10 to which the stacked device 30 is bonded, the solders 16 and 36 do not melt.

The image pickup module 1 has a plurality of bonding portions bonded in different processes, but is easily manufactured and has high reliability of the plurality of bonding portions.

It is preferable that the first member be solder, the second member be solder or a conductive paste, and the third member be a conductive paste because the bonding member is easily selected.

Modifications of First Embodiment

Image pickup modules 1A to 1D of modifications of the first embodiment are similar to the image pickup module 1 and have the same function. Therefore, components having the same functions as those of the image pickup module 1 are denoted by the same reference numerals, and description thereof will be omitted.

Modification 1 of First Embodiment

Figure 4:
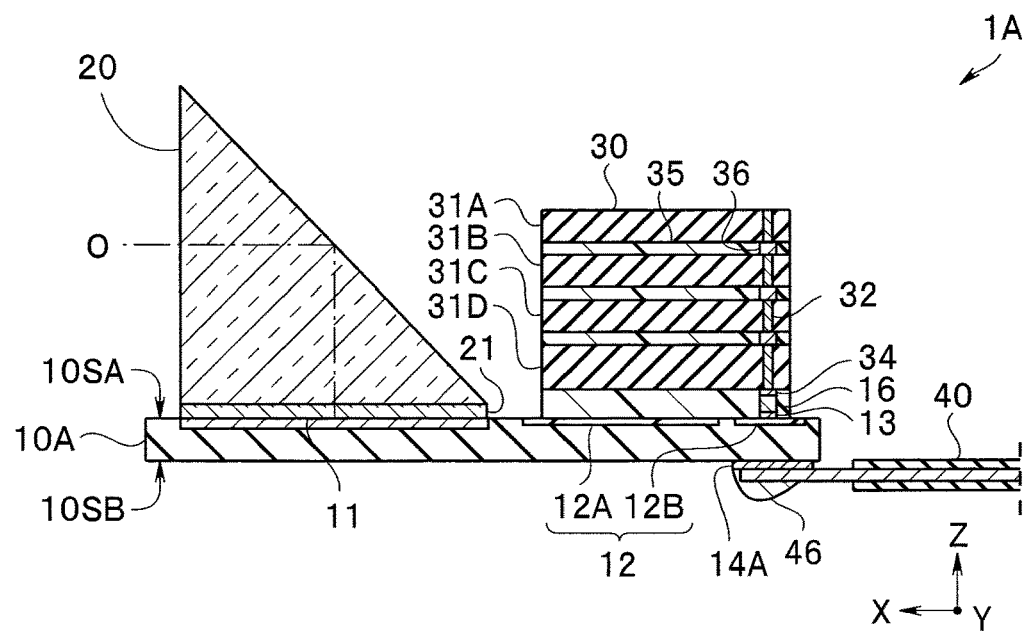
FIG. 4 is a cross-sectional view of an image pickup module according to Modification 1 of the first embodiment.

In the image pickup module 1, the cable 40 is bonded to the second external electrode 14 on the light receiving surface 10SA. On the other hand, in the image pickup module 1A of Modification 1 illustrated in FIG. 4, a third external electrode 14A that is an external electrode is provided on the back surface 10SB of an image pickup device 10A, that is, on the surface opposite to the light receiving surface 10SA on which the peripheral circuit 12 is formed. The cable 40 is bonded to the third external electrode 14A on the back surface 10SB. The third external electrode 14A is electrically connected to the peripheral circuit 12 via a through wiring (not illustrated) of the image pickup device 10A.

The image pickup module 1A is shorter in length in the optical axis direction (X direction) than the image pickup module 1.

Modification 2 of First Embodiment

Figure 5:
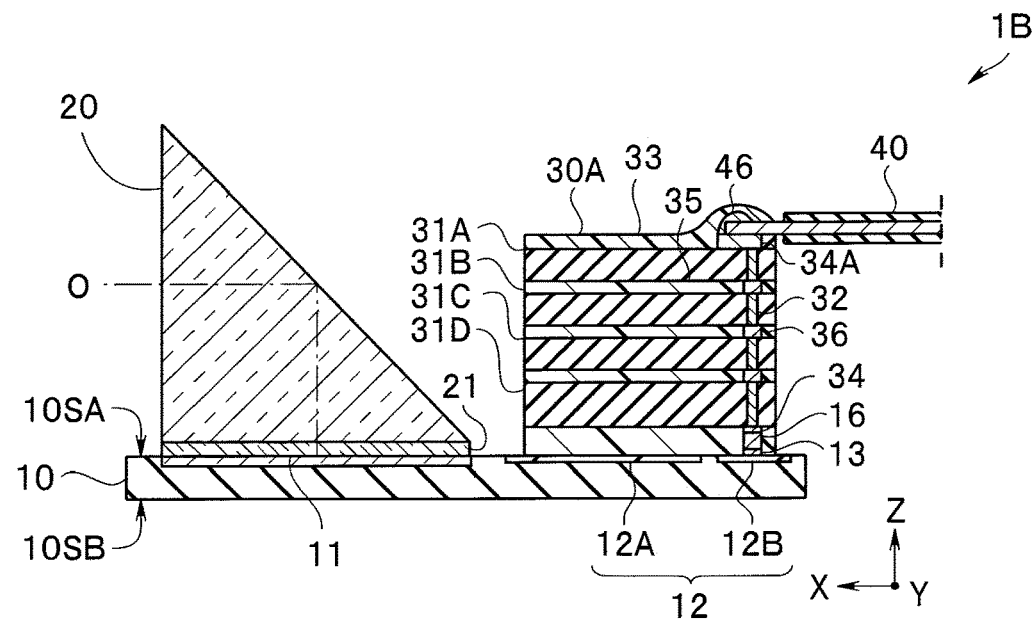
FIG. 5 is a cross-sectional view of an image pickup module according to Modification 2 of the first embodiment.

In the image pickup module 1B of Modification 2 illustrated in FIG. 5, in a stacked device 30A, not only the semiconductor device 31D arranged at the lowermost part has the plurality of bonding electrodes (first bonding electrodes) 34, but also the semiconductor device 31A arranged at the uppermost part has a plurality of second bonding electrodes 34A. The plurality of second bonding electrodes 34A is disposed on the upper surface opposite to the lower surface on which the bonding electrode 34 is disposed. The cable 40 is bonded to the second bonding electrode 34A by the third member such as the conductive paste 46.

The image pickup module 1B is shorter in length in the optical axis direction (X direction) than the image pickup module 1.

It is preferable that a resin layer 33 be stacked on the upper surface of the semiconductor device 31A and the periphery of the second bonding electrode 34A be covered with the resin layer 33. Since the resin layer 33 serves as a wall, the conductive paste 46 that is the third member does not spread around the second bonding electrode 34A. Since stresses applied to the stacked device 30A at the time of cable connection are relaxed by the resin layer 33, the risk of breaking the stacked device 30A is reduced. The resin layer 33 reduces a load applied to the stacked device 30A by tension applied to the cable 40. The image pickup module 1B including the resin layer 33 is easily manufactured and has high reliability. Note that a bonding portion between the second bonding electrode 34A and the cable 40 may also be covered with the resin layer 33. That is, the bonding electrode 34A, a distal end portion of the cable 40, and the conductive paste 46 may be covered with the resin layer 33.

Modification 3 of First Embodiment

Figure 6:
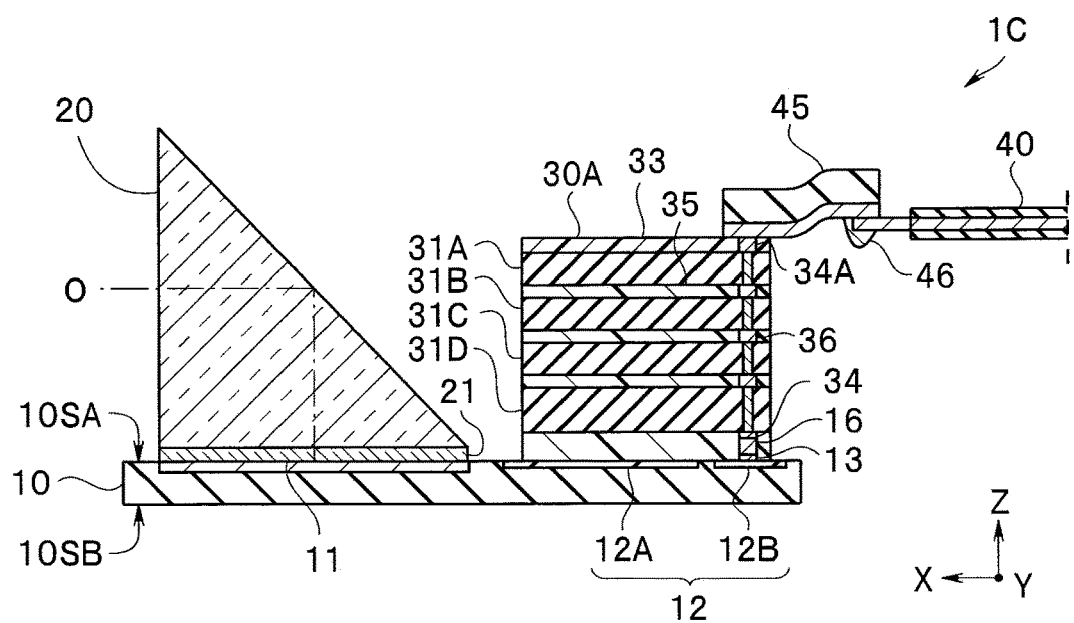
FIG. 6 is a cross-sectional view of an image pickup module according to Modification 3 of the first embodiment.

In an image pickup module 1C of Modification 3 illustrated in FIG. 6, the second bonding electrode 34A of the semiconductor device 31A and the cable 40 are connected via a flexible wiring board 45.

The second bonding electrode 34A is bonded to a first end portion of wiring of the flexible wiring board 45, and the cable 40 is bonded to a second end portion connected to the first end portion. The flexible wiring board 45 has a base made of polyimide or the like, and wiring made of a conductor is disposed on the base. For example, the cable 40 is bonded to the second end portion by the conductive paste 46, and the first end portion of the wiring of the flexible wiring board 45 is ultrasonically bonded to the second bonding electrode 34A of the semiconductor device 31A.

The image pickup module 1C has the effect of the image pickup module 1B, and the stacked device 30A and the cable 40 are easily bonded.

Modification 4 of First Embodiment

Figure 7:
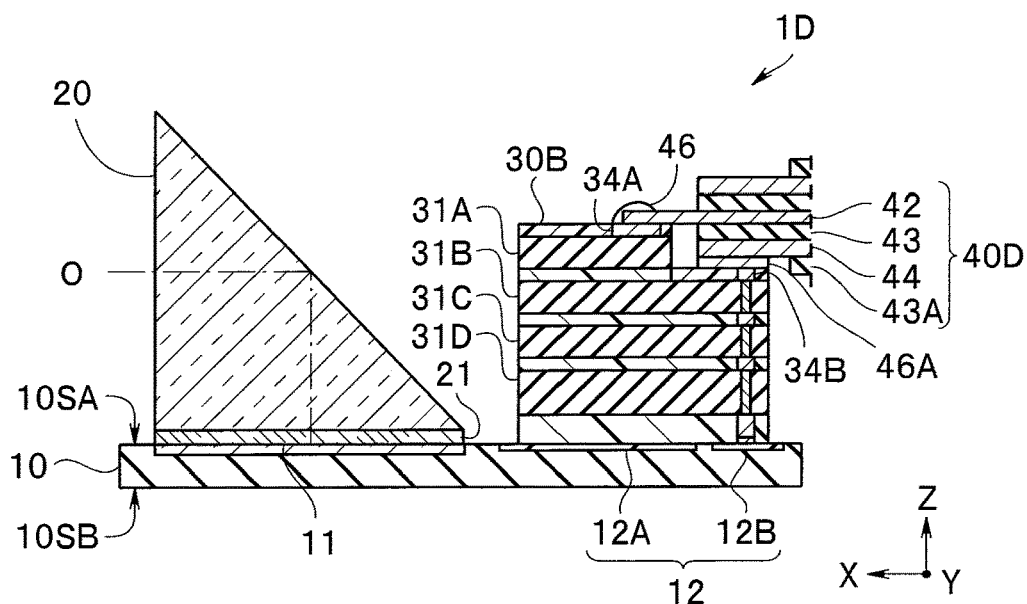
FIG. 7 is a cross-sectional view of an image pickup module according to Modification 4 of the first embodiment.

In the image pickup module 1D of Modification 4 illustrated in FIG. 7, at least any one of a plurality of cables is a shielded cable (coaxial cable) 40D including a core wire 42, an insulating layer 43 coating the core wire, a shielded wire (conductor layer) 44 coating the insulating layer 43, and a casing 43A coating the shielded wire 44.

In a stacked device 30B, an area of the plate-shaped semiconductor device 31A arranged at the uppermost part is smaller than an area of the semiconductor device 31B arranged below the semiconductor device 31A. The upper surface of the stacked device 30B has a step due to the thickness of the semiconductor device 31A. The semiconductor device 31B partially exposed on the upper surface of the stacked device 30B by the step has a bonding electrode 34B.

The core wire 42 of the shielded cable 40D is bonded to the second bonding electrode 34A of the semiconductor device 31A, and the shielded wire 44 is bonded to the bonding electrode 34B of the semiconductor device 31B.

The image pickup module 1D is easily manufactured because the core wire 42 and the shielded wire 44 of the shielded cable 40D are bonded to the stacked device 30B using the step on the upper surface of the stacked device 30B.

Note that the semiconductor device 31A may have the same size as the semiconductor devices 31B to 31D. In the case above, the semiconductor device 31A having the same size as the semiconductor devices 31B to 31D is arranged at a position closer to the prism 20 than the semiconductor device 31B, thereby forming a stepped stacked device in which a part of the semiconductor device 31B is exposed on the upper surface.

Also in the image pickup modules 1B to 1D, the third external electrode 14A to which the cable 40 is bonded may be provided on the back surface 10SB as in the image pickup module 1A. For example, the core wire 42 of the shielded cable 40D may be bonded to the first external electrode 13 on the light receiving surface 10SA, and the shielded wire 44 may be bonded to the third external electrode 14A on the back surface 10SB.

In addition, in the image pickup module 1A, the cable 40 may be bonded to also at least any one of the first external electrode 13 on the light receiving surface and the second bonding electrode 34A of the semiconductor device as in the image pickup modules 1 and 1B to 1D.

In addition, also in the image pickup modules 1, 1A, 1B, and 1D, when the image pickup device 10 or the stacked device 30 and the cable 40 are connected via the flexible wiring board 45, it is needless to say that the same effect as the image pickup module 1C is obtained.

Second Embodiment

An image pickup module 1E of a second embodiment is similar to the image pickup modules 1 and 1A to 1D and has the same function. Therefore, components having the same functions as those of the image pickup module 1 are denoted by the same reference numerals, and description thereof will be omitted.

Figure 8:
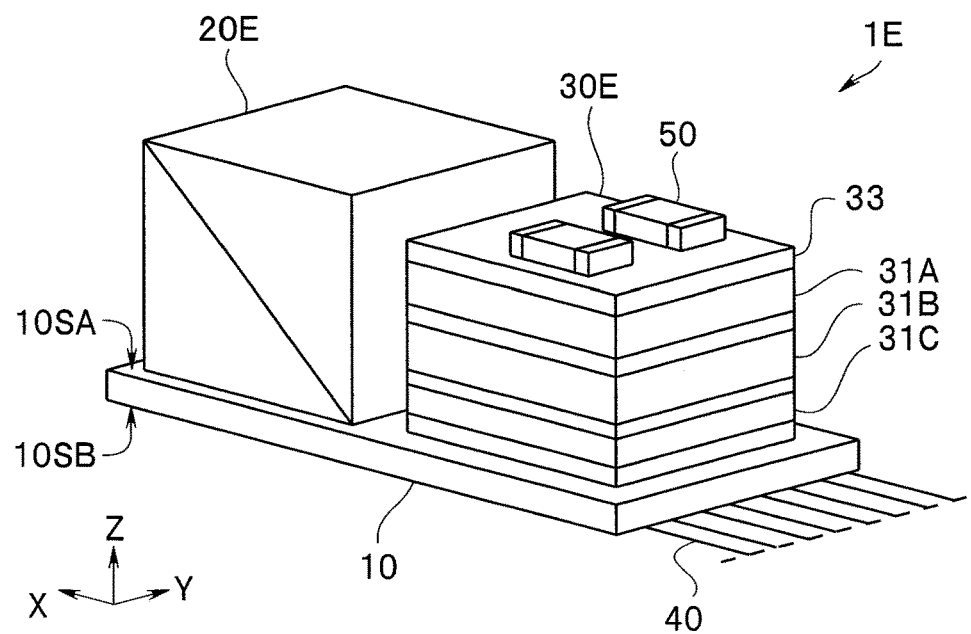
FIG. 8 is a perspective view of an image pickup module according to a second embodiment.

The image pickup module 1E of the second embodiment illustrated in FIG. 8 includes a stacked device 30E in which three semiconductor devices 31A to 31C are stacked. An electronic component 50 is bonded to a bonding electrode (not illustrated) on the upper surface of the stacked device 30E. The electronic component 50 is, for example, a chip component such as a chip capacitor.

In the image pickup module 1E, since the electronic component 50 is disposed in or on the stacked device 30E, for example, the stacked device 30E is easily designed.

Since a height (dimension in the Z-axis direction) of the stacked device 30E in or on which the electronic component 50 is disposed is lower than a height of a prism 20E, a height of the image pickup module 1E is not increased by disposing the electronic component 50.

The prism 20E of the image pickup module 1E has a substantially rectangular parallelepiped shape because a support member is bonded to the reflection surface. The prism 20E is easier to handle than the prism 20. In order to improve the reflectance, a reflective film made of a metal such as aluminum may be disposed on the reflection surface, or an adhesive layer disposed on the reflection surface may be a black film. The prism 20E may be used as the prism of the image pickup modules 1 and 1A to 1D.

Third Embodiment

An image pickup module 1F of a third embodiment is similar to the image pickup modules 1 and 1A to 1E and has the same function. Therefore, components having the same functions as those of the image pickup module 1 are denoted by the same reference numerals, and description thereof will be omitted.

Figure 9:
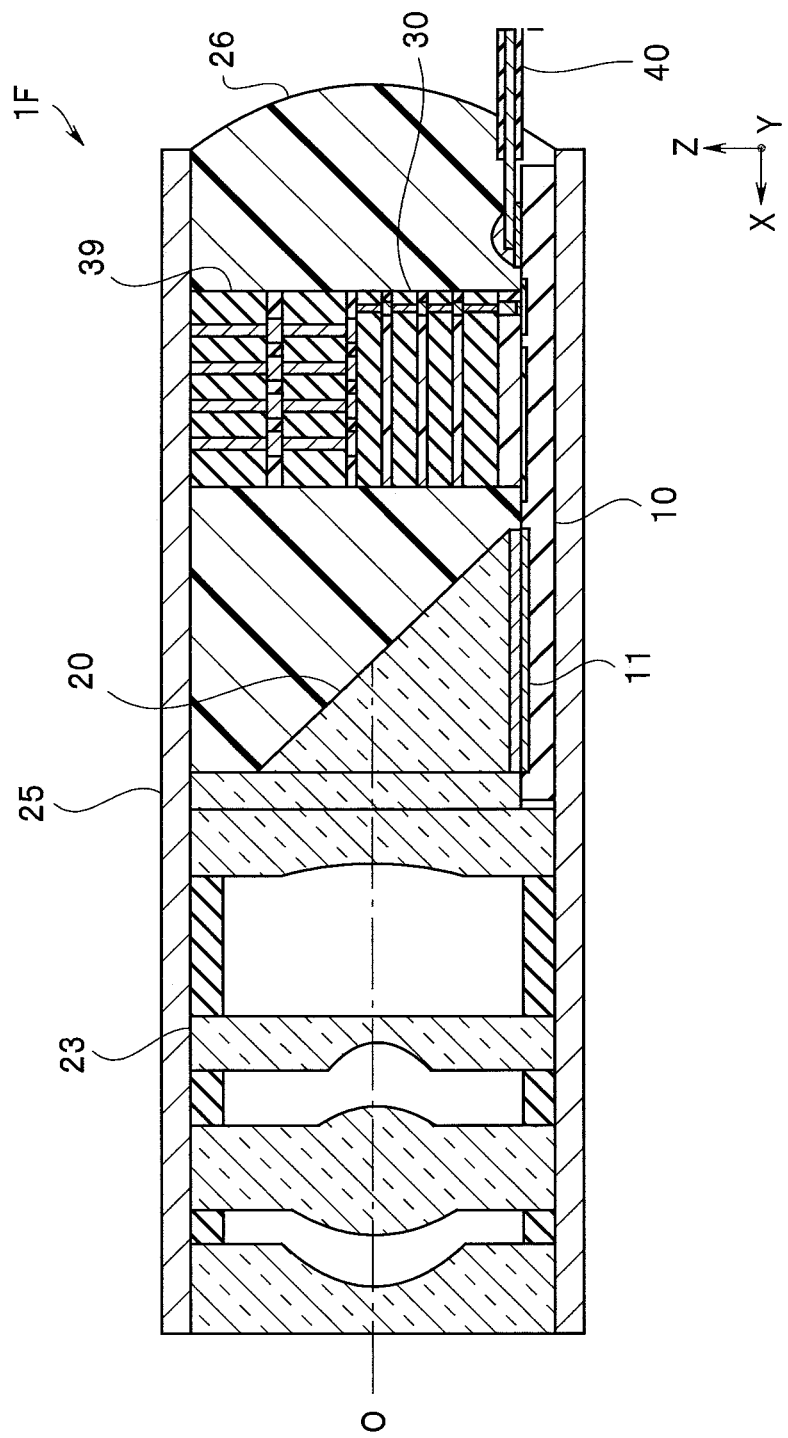
FIG. 9 is a cross-sectional view of an image pickup module according to a third embodiment.

In the image pickup module 1F of the third embodiment illustrated in FIG. 9, a device 39 having a higher thermal conductivity than the stacked device 30 is disposed on the stacked device 30.

In the image pickup module 1F, incident light condensed by the image pickup optical system 23 including a plurality of lenses is guided to a light receiving circuit of the image pickup device 10 by the prism 20. The image pickup module 1F is housed in a pipe 25 made of a metal having high thermal conductivity. The periphery of the image pickup module 1F inside the pipe 25 is filled with a resin 26.

The device 39 is a stacked device in which a plurality of silicon devices each having many through wirings is stacked. Although the device 39 may be a metallic block, it is preferable that the device 39 be made of silicon as a base having the same physical properties such as coefficient of thermal expansion as those of the stacked device 30 including the plurality of semiconductor devices 31 made of silicon as a base, and an area of a region where a semiconductor circuit is formed be smaller than any of the plurality of semiconductor devices 31A to 31D of the stacked device 30. In particular, the device 39 is preferably not provided with a semiconductor circuit. That is, the device 39 has the same silicon as the semiconductor device 31 as a base, but has a larger number of through wirings made of copper or the like than the semiconductor device 31, and thus has higher thermal conductivity than any of the semiconductor devices 31.

Heat generated by the stacked device 30 is transferred to the pipe 25 via the device 39 at least partially in contact with the pipe 25. In the image pickup module 1F, the heat generated by the stacked device 30 is hardly transferred to the image pickup device 10. Therefore, the image pickup module 1F has less thermal noise and high reliability.

It goes without saying that endoscopes 9A to 9F having the image pickup modules 1A to 1F have the respective effects of the image pickup modules 1A to 1F in addition to the effects of the endoscope 9.

The present invention is not limited to the embodiments described above, and various changes, combinations, and applications can be made within a scope without departing from the spirit of the present invention.

What is claimed is:

1. An image pickup module comprising:
    a semiconductor base;
    an image sensor disposed in a first region of the semiconductor base;
    a prism arranged on the image sensor;
    a stacked device comprising a plurality of semiconductor devices each having a through wiring and bonded to each other by solder, the stacked device is disposed on a second region of the semiconductor base, different from the first region;
    a plurality of cables bonded to the stacked device; and
    a resin layer stacked on a first semiconductor device of the plurality of semiconductor devices, the resin layer covering a distal end of each of the plurality of cables, the first semiconductor device is disposed further from the semiconductor base relative to other semiconductor devices of the plurality of semiconductor devices;
    wherein the stacked device includes an electronic component provided on the first semiconductor device.

2. The image pickup module according to claim 1, further comprising:
    a first member that bonds the plurality of semiconductor devices to each other;
    a second member that bonds the stacked device to the semiconductor base; and
    a third member that bonds the plurality of cables to the stacked device, wherein
    a bonding temperature of the first member is higher than a bonding temperature of the second member, and
    a bonding temperature of the second member is higher than a bonding temperature of the third member.

3. The image pickup module according to claim 2, wherein
    the first member is solder,
    the second member is one of solder or a conductive paste, and
    the third member is a conductive paste.

4. An endoscope comprising:
an image pickup module comprising:
a semiconductor base;
an image sensor disposed in a first region of the semiconductor base;
a prism arranged on the image sensor;
a stacked device comprising a plurality of semiconductor devices each having a through wiring and bonded to each other by solder, the stacked device is disposed on a second region of the semiconductor base, different from the first region;
a plurality of cables bonded to the stacked device; and
a resin layer stacked on a first semiconductor device of the plurality of semiconductor devices, the resin layer covering a distal end of each of the plurality of cables, the first semiconductor device is disposed further from the semiconductor base relative to other semiconductor devices of the plurality of semiconductor devices;
wherein the stacked device includes an electronic component provided on the first semiconductor device.

5. The image pickup module according to claim 1, wherein the distal end of each of the plurality of cables is disposed on the through wiring of the first semiconductor device.

6. The image pickup module according to claim 1, wherein the plurality of semiconductor devices are stacked in a direction parallel to a surface of the prism in which light is incident.

7. The image pickup module according to claim 1, wherein the through wiring extends in a direction parallel to a surface of the prism in which light is incident.

8. The endoscope according to claim 4, further comprising an insertion portion extending in a longitudinal axis direction of the insertion portion;
wherein the plurality of semiconductor devices are stacked in the longitudinal axis direction.

9. The endoscope according to claim 4, according to claim 1, further comprising:
a first member that bonds the plurality of semiconductor devices to each other;
a second member that bonds the stacked device to the semiconductor base; and
a third member that bonds the plurality of cables to the stacked device, wherein
a bonding temperature of the first member is higher than a bonding temperature of the second member, and
a bonding temperature of the second member is higher than a bonding temperature of the third member.

10. The endoscope according to claim 9, wherein
the first member is solder,
the second member is one of solder or a conductive paste, and
the third member is a conductive paste.

11. The endoscope according to claim 4, wherein the plurality of semiconductor devices are stacked in a direction parallel to a surface of the prism in which light is incident.

12. The endoscope according to claim 4, wherein the distal end of the cable directly connects to the though wiring exposed on a surface of the first semiconductor device.

13. The endoscope according to claim 4, wherein the through wiring extends in a direction parallel to a surface of the prism in which light is incident.

14. The image pickup module according to claim 1, wherein the distal end of the cable directly connects to the though wiring exposed on a surface of the first semiconductor device.

* * * * *